United States Patent
Palepu

(10) Patent No.: US 7,589,106 B2
(45) Date of Patent: *Sep. 15, 2009

(54) ALCOHOL FREE FORMULATION OF ARGATROBAN

(75) Inventor: Nageswara R. Palepu, South Hampton, PA (US)

(73) Assignee: Eagle Pharmaceuticals, Inc., Woodcliff Lake, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/904,067

(22) Filed: Sep. 26, 2007

(65) Prior Publication Data

US 2008/0076798 A1    Mar. 27, 2008

Related U.S. Application Data

(60) Provisional application No. 60/850,725, filed on Oct. 11, 2006, provisional application No. 60/847,556, filed on Sep. 27, 2006.

(51) Int. Cl.
*A61K 31/4709* (2006.01)
*A61K 31/445* (2006.01)
*A61P 7/02* (2006.01)

(52) U.S. Cl. .................................... 514/314
(58) Field of Classification Search ............. 514/314
See application file for complete search history.

(56) References Cited

U.S. PATENT DOCUMENTS

| | | | |
|---|---|---|---|
| 5,214,052 A | 5/1993 | Ofuchi | |
| 5,506,241 A | 4/1996 | Mano et al. | |
| 5,679,690 A | 10/1997 | Andre et al. | |
| 6,232,315 B1 | 5/2001 | Shafer et al. | |
| 6,495,534 B2 | 12/2002 | Colombo et al. | |
| 2004/0242582 A1 | 12/2004 | Green et al. | |
| 2007/0049617 A1 | 3/2007 | Owoo | |

FOREIGN PATENT DOCUMENTS

| | | |
|---|---|---|
| EP | 0608828 | 1/1994 |
| EP | 0608831 | 3/1994 |
| EP | 0621036 | 4/1994 |
| WO | 2004-026252 | 4/2004 |

OTHER PUBLICATIONS

Solomon, Seth Aqueous Humor Dynamics, Revised 2002, pp. 1-17.*
Abstract of JP 56015267A Feb. 14, 1981 (equivalent to JP 1382377C Jun. 9, 1987).
International Search Report and Written Opinion of the International Searching Authority from related PCT/US2007/20725 (11 pg).
International Search Report and Written Opinion of the International Searching Authority from related PCT/US2007/21533(9 pg).

* cited by examiner

*Primary Examiner*—Sharmila Gollamudi Landau
*Assistant Examiner*—Kortney L Klinkel
(74) *Attorney, Agent, or Firm*—Lucas & Mercanti, LLP

(57) ABSTRACT

An aqueous formulation of argatroban and of related compounds is disclosed along with a reconstitutable formulation, each of which is substantially, if not totally alcohol free. The formulations are also substantially free, if not totally free, of mono-, di-, and oligo-saccharides. An especially preferred embodiment is a ready-to-administer 1 mg/ml injectable dosage form having argatroban, lactobionic acid, and methionine.

23 Claims, No Drawings

US 7,589,106 B2

ALCOHOL FREE FORMULATION OF ARGATROBAN

CROSS-REFERENCE TO RELATED APPLICATIONS

This application claims the benefit of priority of U.S. Provisional Application Ser. No. 60/850/725, filed Oct. 11, 2006 and U.S. Provisional Application Ser. No. 60/847,556, filed Sep. 27, 2006. Reference is also made to co-owned PCT application filed concurrently herewith having the same title and inventorship as the instant application and claiming priority from the same two provisional applications above. Each of these applications as well as each patent and patent application mentioned in the rest of this specification is incorporated herein by reference in their entireties.

STATEMENT REGARDING FEDERALLY SPONSORED RESEARCH OR DEVELOPMENT

Not Applicable

FIELD OF THE INVENTION

The present invention relates to argatroban and to the solubilization thereof to yield injectable and other aqueous solutions of desired concentration in aqueous media without the need for alcohols or other solvents and without the use of saccharides.

BACKGROUND OF THE INVENTION

Argininesulfonamides are known to have anti-thrombotic activities (see e.g., Japanese Patent No. 1382377). However, it is very difficult to obtain a solution containing any of the argininesulfonamides at high concentrations due to their general poor solubility in water. Therefore these compounds are generally not suitable for use in injection formulations containing them at high concentrations. U.S. Pat. No. 5,214,052 attempts to solve this problem by dissolving these compounds in a dissolution media containing water, ethanol, and a saccharide (inclusive of monosaccharides, disaccharides, oligosaccharides and their reduced sugar alcohol counterparts). Argatroban, currently marketed by Encysive in the U.S., is sold as a 2.5 ml vial of 100 mg/ml argatroban concentrate having 750 mg D-sorbitol, and 1000 mg dehydrated alcohol per ml, which concentrate is subsequently diluted to 1 mg/ml argatroban for actual use. While that formulation allows for advantages in packaging and dissolution to final concentration, it suffers from the drawback of having ethanol present in a not insignificant amount, especially when the patient in question is of smaller body weight. Current administration rates include 6 ml/hr (of the 1 mg/ml diluted solution) for a 50 kg patient to 17 ml/hr (of the 1 mg/ml diluted solution) for a 140 kg patient each for the duration of the procedure for which argatroban administration is desired. Thus, each vial supplied provides 250 ml of administrable diluted solution, resulting in substantial waste of material in all but the most prolonged procedures (250 ml being sufficient for over 40 hours for a 50 kg patient and over 14 hours for a 140 kg patient).

OBJECT OF THE INVENTION

An object of the invention is to provide a method for improving the solubility of argatroban in a completely aqueous system, in particular avoiding the use of organic solvents such as monoalcohols of 1-4 carbon atoms, especially ethanol, and still obtain solutions of sufficient concentration for use in parenteral administration.

A further object of the invention is to provide an argatroban formulation that is substantially free of saccharides, inclusive of mono-saccharides, di-saccharides, oligosaccharides, and their corresponding sugar alcohols.

Another object of the invention is to provide a dosage form of argatroban that is not as concentrated so that further dilution for use does not result in substantial waste of material in most typical administration settings.

A further object of the invention is to provide a dosage form of argatroban not requiring an extensively large dilution, yet be concentrated sufficiently to be convenient for preparing for use and less subject to dissolution errors than with current marketed argatroban.

Still a further object of the invention is to provide 1 mg/ml ready-to-administer solutions of argatroban in 5 ml to 500 ml vials and 25 ml to 500 ml infusion bags.

Yet another object of the invention is to provide an argatroban ready-to-administer formulation having a storage stability of at least about 18 months.

Still another object of the invention is to provide an argatroban ready-to-administer formulation having a substantial stability with respect to pH in a terminal sterilization operation.

An even further object of the invention is to provide an argatroban ready-to-administer formulation having a substantial stability with respect to degradation product in a terminal sterilization operation.

An even further object of the invention is to provide an argatroban ready-to-administer formulation having a substantial stability with respect to degradation product in the presence of an antioxidizing agent such as methionine in an aseptic operation or in a terminal sterilization operation.

Still another object of the invention is the use of lactobionic acid as a solubilizer and/or stabilizer to enhance the aqueous solubility as well as stability of argatroban.

Yet another object of the invention is to provide an argatroban ready-to-administer aqueous solution for injection having carbonate and/or bicarbonate ion present.

Yet further objects of the invention will be apparent to those of ordinary skill in the art.

SUMMARY OF THE INVENTION

The invention provides a method for dissolving argatroban comprising dissolving argatroban or a pharmaceutically acceptable salt thereof in an aqueous buffer system that is substantially free of lower alcohols and is substantially free of saccharides (e.g., mono-, di-, and oligo-saccharides and their corresponding sugar alcohols). Further, the invention provides pharmaceutical compositions containing argatroban.

DETAILED DESCRIPTION OF THE INVENTION

In certain embodiments, the invention provides a method for dissolving argatroban comprising dissolving an $N^2$-arylsulfonyl-L-arginine having general formula (I) or a pharmaceutically acceptable salt thereof

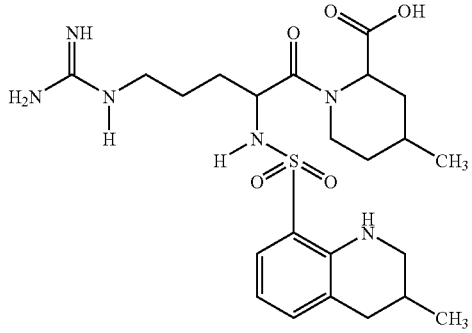

(I)

The compound exists as isomers and for purposes of this application, reference to "argatroban" (unless indicated or the context requires otherwise) refers to the individual isomers as well as the various mixtures of isomers in various proportions. Currently marketed argatroban has the chemical name set forth in its labeling as (2R,4R)-1-[$N^2$-(3-methyl-1,2,3,4-tetrahydro-8-quinoline-sulfonyl)-L-arginyl]-4-methyl-2-piperidinecarboxylic acid. Further, unless indicated otherwise or the context requires otherwise, reference to "argatroban" includes reference to the various pharmaceutically acceptable salts thereof, whether salts thereof with acids or bases.

The invention can use the pharmaceutically acceptable salts of argatroban. The salts may be acid addition salts (there being a free carboxy group present) prepared by reacting the argatroban or a different salt thereof (inclusive of (a) pharmaceutically acceptable salts other than the salt being made and (b) pharmaceutically unacceptable salts) with any pharmaceutically acceptable inorganic or organic acid such as, without limitation, hydrochloric acid, hydrobromic acid, hydroiodic acid, sulfuric acid, nitric acid, phosphoric acid, carbonic acid, acetic acid, citric acid, maleic acid, succinic acid, lactic acid, tartaric acid, gluconic acid, glucuronic acid, ethers of glucuronic acid or gluconic acid (such as lactobionic acid), benzoic acid, methanesulfonic acid, ethanesulfonic acid, benzenesulfonic acid and p-toluenesulfonic acid. Further, the salts may be inorganic or organic salts prepared by reacting the argininesulfonamide of general formula (I) with any pharmaceutically acceptable organic or inorganic bases such as sodium hydroxide, potassium hydroxide, ammonium hydroxide, sodium bicarbonate, sodium carbonate, potassium bicarbonate, potassium carbonate, ammonium bicarbonate, ammonium carbonate, triethylamine, procaine, dibenzylamine, N,N'-dibenzylethylenediamine and N-ethylpiperidine.

In one method for dissolving argatroban according to the invention, the argatroban and/or its salt is dissolved in an amino acid aqueous solution. The amino acid used in the invention is preferably selected from arginine, glycine, methionine, or other amino acids with at least one basic group pKa>9.0 or mixtures thereof. The amino acid can be used as the acid or a salt thereof or mixtures thereof. While either D- or L- or D,L-amino acids can be used, L-amino acids are generally preferred in this first embodiment. In another embodiment, discussed below, D,L-amino acids are generally preferred. The pH of the drug and amino acid solution is adjusted to about 8.0 to about 10.0 with one or more pharmaceutically acceptable carboxylic acids such as, without limitation, acetic acid or any other carboxylic acid or dicarboxylic acid or hydroxy carboxylic acid; and may be adjusted with either the acid itself, or a salt thereof, or mixtures thereof if an appropriate pH can be reached using such salt or mixture of salt and acid. More highly preferred amino acids are arginine, glycine, and methionine. In this first embodiment, arginine and glycine are even more highly preferred, while in a second embodiment discussed more specifically below, methionine is an even more highly preferred amino acid.

In the present invention, reference to a given weight of a compound that can exist as a salt or in free form is with reference to the free form of the compound. Thus, for a compound such as argatroban having a molecular weight of 526 g, and monosodium argatroban having a molecular weight of 548 Dalton, and argatroban monohydrochloride having a molecular weight of 561 Dalton, an indication of "52.6 mg of argatroban" will mean 52.6 mg of argatroban non-salt form, or if the monosodium salt is being discussed, 52.6 mg of argatroban will mean 54.8 mg of monosodium argatroban having 52.6 mg of the argatroban moiety present, or if the argatroban monohydrochlodride is being discussed, it will mean 56.1 mg of argatroban monohydrochloride having 52.6 mg of the argatroban non-salt moiety present. Corresponding calculations to find the exact weight of the salt form under discussion for other salts are known to those of ordinary skill in the art. Weights of amino acids will also be referenced to the non-salt forms thereof with appropriate calculations to find the precise weight of a particular salt being known to those of ordinary skill in the art.

The amino acid is generally present in amounts that are about 1.5 to about 2.5, preferably about 2 times the amount of the compound of formula (I) present (based on the non-salt form of argatroban). The carboxylic acid (other than carbonic acid salt) is generally present in amounts that are about 1.5 to about 2.5, preferably about 2 times the amount of argatroban present (based on the argatroban moiety), while the carbonic acid salt is generally present in an amount of about 1.4 to about 5.2 (based on $CO_3$ content) times the amount of argatroban present (based on the argatroban moiety), preferably about 1.5 to about 2.5 times, more preferably about 1.9 to about 2.0 times when the amino acid is absent and preferably about 3.0 to about 5.2 times, more preferably about 4.1 to about 4.2 times when the amino acid is present. Those of ordinary skill in the art will be able to adjust these amounts for the situation where both a carboxylic acid (other than carbonic acid salt) is present in combination with a carbonic acid salt.

Water as used in the present invention (unless indicated otherwise or the context requires otherwise) includes aqueous injectable fluids including, but not limited to, distilled water, purified water, water for injection, a physiological saline, Ringer's Solution, Lactated Ringer's Solution and 5% dextrose solution.

The manner of how to dissolve the argatroban in water and optionally in an amino acid aqueous solution is not particularly limited. Generally, the amino acid (or its salt or a mixture of the amino acid and its salt), when present, is dissolved in water and then the pH is adjusted upward, if need be, to about pH 8.7 to about 10 with the addition of inorganic or organic base (or salts of carboxylic acid or mixtures of its salts and their conjugate acids or conjugate bases (inclusive of alkali metal salt(s) and ammonium salts of carbonic acid)) thereto followed by mixing. These two steps can be reversed if desired. Next, the argatroban is slowly added while stirring until complete dissolution. If desired, but not required, the pH can then be adjusted downward using any suitable inorganic or organic acid or buffer thereof. Where concentrates are to be made for subsequent dilution, higher pH can be tolerated for the dissolution and storage phase as the subsequent dilution will bring the pH closer to physiologic pH before injection.

Concentrates having the amino acid in the range of 50 mg/ml (especially when using arginine as the amino acid) will have a pH as high as about 11 to about 11.5 before addition of the argatroban. In these concentrates, the argatroban is dissolved and the pH is adjusted downward into the range of about 8.7 to 9.5 as discussed above using an appropriate acid or buffer. Where a ready-to-administer injection formulation is desired, the ready-to-administer product pH should generally not be greater than about pH about 9.2, and more preferably is usually about pH 8.7, about 8.8, or about 8.9.

The temperature on dissolution is not particularly limited. When the argatroban is dissolved in water, however, it is preferable to warm the water to about 40° C. to about 70° C. for accelerating the dissolution rate.

The concentration of argatroban in the solution can be selected within a wide range depending on the intended uses. According to the invention, the solution in which the argatroban is dissolved may result in concentrations of argatroban that are several fold higher than the concentrations of argatroban typically obtained with the solubility of argatroban in water alone. Most advantageously for the present invention, the argatroban can be dissolved up to about 7.5 mg/ml, preferably about 6 mg/ml, most preferably about 5 mg/ml. An additional embodiment within the invention is a ready-to-administer solution of about 0.8 to about 1.25 mg/ml, preferably about 0.9 to about 1.1 mg/ml, more preferably about 1 mg/ml argatroban. All amounts presented are amounts of argatroban free compound that is the non-salt. Corresponding amounts of various salts will be readily known to those of ordinary skill in the art by routine calculation.

In a second embodiment of the invention, the argatroban, or a pharmaceutically acceptable salt thereof, is dissolved in an aqueous solution of a gluconic or glucuronic acid (or a sugar ether of either, where the sugar position 1 is etherified with one of the hydroxyl groups of the gluconic or glucuronic acid, preferably the ether is lactobionic acid or a salt thereof) and/or with an alkali metal salt, preferably a sodium salt, of carbonic acid (e.g., sodium carbonate, sodium bicarbonate, and mixtures thereof) and optionally an amino acid or salt thereof. In each case, the salts, if present are pharmaceutically acceptable salts, and in the case of use of the solution as an injectable, the salt is compatible with its use in an injectable formulation. Preferably, the formulation comprises argatroban or a pharmaceutically acceptable salt thereof; a gluconic acid or glucuronic acid, or an ether of either or a pharmaceutically acceptable salt thereof (preferably lactobionic acid or a pharmaceutically acceptable salt thereof) and/or an alkali metal salt of carbonic acid, preferably a sodium salt of carbonic acid or mixture of sodium salts of carbonic acid; optionally an amino acid, preferably an anti-oxidant amino acid (more preferably methionine), arginine, or glycine, either in the D-, L-, or D,L-form, preferably as the D,L-form, the amino acid optionally in the form of a pharmaceutically acceptable salt thereof; and water (which water may further contain an optional inert osmolarity adjuster (other than a saccharide) so as to bring the solution to an appropriate osmolarity if desired); and wherein the formulation is substantially free of ethanol, preferably in the substantially free of monohydric alcohols having 1 to 4 carbons; and further, the formulation being substantially free of mono-, di-, and oligosaccharides and their corresponding sugar alcohols. For the present invention, "substantial free" when referring to a lower alcohol means less than about 5% v/v, preferably less than about 2.5%, more preferably less than about 1%, more preferably less than about 0.5% v/v; while when referring to "saccharide" means less than about 10% w/v, preferably less than about 7.5%, more preferably less than about 5%, still more preferably less than about 2.5%, even more preferably less than about 1%, yet more preferably less than about 0.05% w/v. Inclusion of methionine or another anti-oxidant amino acid improves the product stability especially with respect to terminal sterilization, and is therefore one particularly preferred embodiment.

In this embodiment, it is preferable to first heat the water, preferably to boiling, then allow the water to cool to a temperature of about 30-50° C., preferably about 35° C. The carboxylic acid (preferably lactobionic acid or pharmaceutically acceptable salt thereof and/or alkali metal or ammonium salt of carbonic acid) is added and dissolved. Then, any optional amino acid is added and dissolved. Then the argatroban (or a pharmaceutically acceptable salt thereof) is added and dissolved. In this procedure, the amino acid and carboxylic acid addition steps can be reversed, if desired, or the amino acid can be added after the argatroban. The pH is adjusted as convenient at any point prior to the addition of the compound of formula (I) or pharmaceutically acceptable salt thereof to a pH in excess of about 8.5, preferably in excess of about 8.6, more preferably to about pH 8.7 to about 9.2, still more preferably about 8.7, about 8.8, about 8.9, about 9.0, about 9.1 or about 9.2, so as to aid in the dissolution of the compound of formula (I).

Higher pH's are acceptable for the dissolution phase for concentrate formulations that will be further diluted before actual injection, provided the dilution brings down the pH to a range such that upon dilution to the final use concentration the pH is physiologically acceptable for injection purposes, typically less than about 9.2, preferably less than about 9.0, more preferably less than about 8.8, still more preferably about 8.7. If need be, final adjustment of pH can be made with an acid or base or buffer as appropriate such as hydrochloric acid, sodium hydroxide, or a buffer solution of either or both the carboxylic acid/carboxylic acid salt (inclusive of blends of alkali metal or ammonium salts of carbonic acid) and/or the amino acid/amino acid salt. Thus, a concentrate formulation may be prepared within the instant invention which has a substantially high pH, while the ready-to-administer formulations will have a generally weakly alkaline pH, generally greater than about 8.6 and generally less than about 9.2.

The solution thus obtained containing the argatroban, amino acid, water and carboxylic acid constitutes a first embodiment of the pharmaceutical composition of the invention, while the solution containing (a) the argatroban; (b) water; (c) (1) gluconic acid, glucuronic acid, and/or ether thereof, and/or (c) (2) an alkali metal or ammonium salt or mixtures of alkali metal or ammonium salts of carbonic acid; and (d) optional (preferably anti-oxidant) amino acid constitutes a second embodiment. As will be readily recognized, these two embodiments overlap when the carboxylic acid in the first embodiment is selected from gluconic acid, glucuronic acid, the ether of either (especially lactobionic acid) and alkali metal salt or mixture of alkali metal salts of carbonic acid; and the amino acid in the first embodiment is an anti-oxidant amino acid.

The pharmaceutical compositions of the invention are useful for treating thrombosis and for treating and/or prophylaxis of any other condition for which the active agents are already known to be useful. Accordingly, the pharmaceutical compositions can be used as anti-thrombotic agents.

The pharmaceutical composition of the invention may contain antiseptic, anti-oxidant, soothing agents and the like. If necessary, any pharmaceutical ingredient(s) other than the argatroban may be added to form a combined preparation, provided such other ingredient is not unacceptable for the indication and route of administration; however, the invention compositions and processes are substantially free of, if not totally free of (1) ethyl alcohol or (2) a saccharide, preferably a monosaccharide or disaccharide or oligo-saccharide, more preferably any saccharide (wherein saccharide herein optionally includes the reduced sugar alcohol counterparts thereto), or (3) both (1) and (2).

The primary composition of the invention in the first embodiment is a pharmaceutical injectable and is administered as an injection. This injectable composition may further contain stabilizer, buffer, preservative and the like that are acceptable for injection. If desired, the injectable composition according to the invention is prepared to contain argatroban at a high concentration, which is used by diluting with water, electrolyte (e.g., normal saline, among others), carbohydrate solution (e.g., 5% Dextrose), Ringer's solution or the like at or close to the time of administration (such as by infusion and/or dialysis). The concentrated formulation may contain amounts of up to about 7.5 mg argatroban moiety, preferably up to about 5 mg per ml. This is generally diluted for administration to about 1 mg argatroban moiety per ml. Dilution of the concentrate to other concentrations for use as an injection will be within the ordinary skill in the art. The formulation, as detailed further below, can also be prepared as a lyophilizate or as a sterile dry fill product that can be reconstituted with appropriate diluent.

The primary composition of the invention second embodiment is also as a pharmaceutically acceptable injection formulation, primarily as a ready-to-administer composition. In this embodiment, the argatroban moiety is present in a concentration of no more than about 1.25 mg/ml, preferably about 1.1 mg/ml, more preferably about 1 mg/ml, in a pH of about 8.5 to about 9.2, preferably about 8.6 to about 8.9, more preferably about pH 8.7 to about 8.9 water solution containing (a) as a carboxylic acid, at least one member selected from (1) gluconic acid, glucuronic acid, and sugar ethers thereof, especially lactobionic acid and pharmaceutically acceptable salts thereof and/or (2) alkali metal or ammonium salt or mixture of alkali metal or ammonium salts of carbonic acid, and optionally (b) at least one (preferably anti-oxidant) amino acid or pharmaceutically acceptable salt thereof. If the free argatroban concentration is greater than about 1.0 mg/ml, the concentrate can be diluted with sufficient water of a suitable pH, with or without the amino acid or the carboxylic acid. In embodiments in which an osmotic adjuster material is utilized (other than as part of dilution at the point of administration), the osmotic adjuster is not a saccharide or sugar alcohol.

EXAMPLES

The invention will now be further described by the following, non-limiting examples.

Example 1

(2R,4R)-1-[N$^2$-(3-methyl-1,2,3,4-tetrahydro-8-quinolinesulfonyl)-L-arginyl]-4-methyl-2-piperidinecarboxylic acid (argatroban) was dissolved (to a concentration of 5 mg/ml) in an aqueous system containing 50 mg/ml arginine with pH of the final solution adjusted to 9.0 with acetic acid. The dissolution of argatroban was carried out at 25° C.

Example 2

Argatroban is dissolved (to a concentration of 5 mg/ml) in an aqueous system containing 50 mg/ml arginine with pH adjusted to 9.0 with acetic acid. The dissolution of argatroban is carried out at 50° C.

Example 3

Argatroban is dissolved (to a concentration of 5 mg/ml) in an aqueous system containing 50 mg/ml arginine with pH adjusted to 9.0 with tartaric acid. The dissolution of argatroban is carried out at 25° C.

Example 4

Argatroban is dissolved (to a concentration of 5 mg/ml) in an aqueous system containing 50 mg/ml arginine with pH adjusted to 9.0 with citric acid. The dissolution of argatroban is carried out at 25° C.

Example 5

Argatroban is dissolved (to a concentration of 5 mg/ml) in an aqueous system containing 50 mg/ml arginine with pH adjusted to 9.0 with adipic acid. The dissolution of argatroban is carried out at 25° C.

Example 6

Argatroban is dissolved (to a concentration of 5 mg/ml) in an aqueous system containing 50 mg/ml lysine with pH adjusted to 9.0 with acetic acid. The dissolution of argatroban is carried out at 25° C.

Example 7

Argatroban is dissolved (to a concentration of 5 mg/ml) in an aqueous system containing 50 mg/ml arginine with pH adjusted to 10.0 with acetic acid. The dissolution of argatroban is carried out at 25° C.

Example 8

Argatroban is dissolved (to a concentration of 5 mg/ml) in an aqueous system containing 50 mg/ml arginine with pH adjusted to 8.0 with acetic acid. The dissolution of argatroban is carried out at 25° C.

Example 9

Examples 1-8 are repeated except that the dissolution is carried out at the following concentrations (based on argatroban non-salt form) using the temperatures and form of argatroban as indicated:

| Form | Concentration of argatroban moiety | Temperature |
| --- | --- | --- |
| Non-salt | 5 mg/ml | 15° C. |
| Non-salt | 5 mg/ml | 20° C. |
| Non-salt | 5 mg/ml | 30° C. |
| Non-salt | 5 mg/ml | 35° C. |
| Non-salt | 7.5 mg/ml | 15° C. |
| Non-salt | 7.5 mg/ml | 20° C. |
| Non-salt | 7.5 mg/ml | 30° C. |
| Non-salt | 7.5 mg/ml | 35° C. |
| Sodium Salt | 5 mg/ml | 15° C. |
| Sodium Salt | 5 mg/ml | 20° C. |
| Sodium Salt | 5 mg/ml | 25° C. |
| Sodium Salt | 5 mg/ml | 30° C. |
| Sodium Salt | 5 mg/ml | 35° C. |
| Sodium Salt | 7.5 mg/ml | 15° C. |
| Sodium Salt | 7.5 mg/ml | 20° C. |

-continued

| Form | Concentration of argatroban moiety | Temperature |
|---|---|---|
| Sodium Salt | 7.5 mg/ml | 25° C. |
| Sodium Salt | 7.5 mg/ml | 30° C. |
| Sodium Salt | 7.5 mg/ml | 35° C. |
| Hydrochloride salt | 5 mg/ml | 15° C. |
| Hydrochloride salt | 5 mg/ml | 20° C. |
| Hydrochloride salt | 5 mg/ml | 25° C. |
| Hydrochloride salt | 5 mg/ml | 30° C. |
| Hydrochloride salt | 5 mg/ml | 35° C. |
| Hydrochloride salt | 7.5 mg/ml | 15° C. |
| Hydrochloride salt | 7.5 mg/ml | 20° C. |
| Hydrochloride salt | 7.5 mg/ml | 25° C. |
| Hydrochloride salt | 7.5 mg/ml | 30° C. |
| Hydrochloride salt | 7.5 mg/ml | 35° C. |

Example 10

6 vials of 5 mg/ml argatroban solution of Example 1 are diluted to 1 mg/ml for a total of 30 ml of 1 mg/ml solution and used to administer the same to a 50 kg patient at the rate of 6 mg/hour for a procedure expected to be 4.5 hours. Upon completion of the procedure, there is a minimal amount of unused drug (less than 5 mg) as compared with over 200 mg that would result from the currently marketed argatroban 100 mg/ml 2.5 ml vials.

Attempts to use partial vials of the currently marketed 100 mg/ml 2.5 ml vial to dilute only 30 mg (0.3 ml) yield variations in actual amounts withdrawn for subsequent dilution and are thus not as reliable as using complete 5 mg/ml vials of the present invention.

Example 11

Water is heated to boiling and allowed to cool to about 35° C. Lactobionic acid is added thereto in an amount to achieve a concentration of about 2 mg/ml. Argatroban is then added thereto in an amount sufficient to achieve a concentration of about 1 mg/ml. The solution is packaged in appropriate containers as a ready-to use injectable and the completed packages are terminally heat sterilized.

Example 12

Example 11 is repeated except that the solution pH is adjusted to about 8.7 after addition of the lactobionic acid, but before the addition of the argatroban.

Example 13

Example 11 is repeated except that the amounts of lactobionic acid and argatroban are increased by an additional 10% and after the argatroban has been dissolved, optionally additional water at pH about 8.7 is added to bring the final concentration of argatroban to about 1 mg/ml and the final concentration of lactobionic acid to about 2 mg/ml.

Examples 14

Water was heated to boiling and allowed to cool to about 35° C. D,L-methionine was added to arrive at a methionine moiety concentration of about 2 mg/ml. Lactobionic acid was then added in an amount to achieve a concentration of about 2 mg/ml. Argatroban was then added thereto in an amount sufficient to achieve a concentration of about 1 mg/ml. The solution was packaged in appropriate containers as a ready-to use injectable and the completed packages were terminally heat sterilized.

Examples 15-16

Examples 12-13 are repeated except that in Examples 15-16, DL-methionine is added before the lactobionic acid.

Examples 17-22

Examples 11-13 are repeated except that in Examples 17-19, DL-methionine is added after the lactobionic acid, but before the argatroban; and in Examples 20-22, D,L-methionine is added after the argatroban, in each of Examples 20-22 in an amount to result in a concentration of about 2 mg/ml D,L-methionine, and in Examples 17-19 in an amount of about 10% greater than in Examples 20-22.

Example 23

11 mg of argatroban was dissolved in 2.6 ml of 0.025N sodium carbonate and the pH was adjusted with the addition of 1.5 ml of 0.025N HCl. Sufficient water for injection was added to bring the final solution volume to 10 ml, which had a pH of about 9.12.

Examples 24-25

11 mg of argatroban is dissolved in 5.5 ml of 0.025N sodium carbonate. In Example 24, 20 mg of D,L-methionine is added and then the pH is adjusted downward with 1.5 ml of 0.025N HCl. In Example 25, these two steps are reversed. Water for injection is then added in a sufficient quantity to bring the final volume to 10 ml, which final solution has a pH of about 8.85.

Example 26

Glycine was dissolved in water in an amount sufficient to achieve a glycine moiety final concentration of 2 mg/ml. The pH was then adjusted with 1N sodium hydroxide to about 9.2. Sufficient argatroban was added thereto to result in a final argatroban moiety concentration of about 1 mg/ml. The final pH was adjusted, if needed, to about 9.2 with 1N sodium hydroxide.

Examples 27-31

Example 26 is repeated except that lactobionic acid is added in an amount to result in a final lactobionic acid concentration of about 2 mg/ml after the glycine is dissolved but before the pH is adjusted, and the pH is adjusted to 8.5 (Example 27), 8.7 (Example 28), 9.0 (Example 29), 9.5 (Example 30), or 10.0 (Example 31).

The invention claimed is:

1. A pharmaceutically acceptable formulation of the compound of formula I or a pharmaceutically acceptable salt thereof, which is solubilized in an aqueous solution, said formulation comprising (a) argatroban of formula I or a pharmaceutically acceptable salt thereof

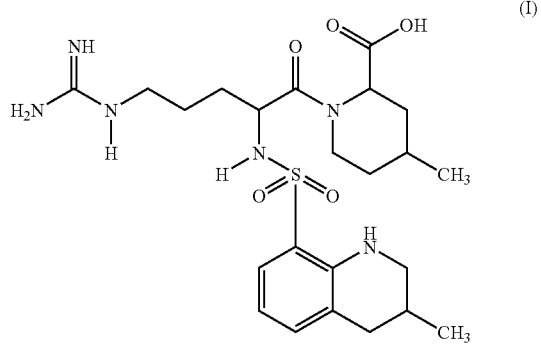

(b) methionine, pharmaceutically acceptable salts thereof, and mixtures thereof;
(c) a member selected from the group consisting of one or more non-amino acid pH adjusting organic acids, organic bases, inorganic acids or inorganic bases, or salts thereof and mixtures thereof; and
(d) a member selected from the group consisting of lactobionic acid and pharmaceutically acceptable salts thereof, which formulation is substantially free of ethanol and substantially free of a sugar alcohol and has a pH in excess of 8.5.

2. The formulation of claim 1 in which said argatroban is present in a concentration equivalent to an amount (based on the argatroban moiety) selected from the group consisting of: about 1 mg/ml, about 1.25 mg/ml, about 2 mg/ml, about 2.5 mg/ml or about 5 mg/ml.

3. The formulation of claim 1 wherein said member (e) is at least one member selected from the group consisting of (1) a carboxylic acid, a hydroxy carboxylic acid, a dicarboxylic acid, with at least one of its acid group pKa(s) greater than 3.0, a salt thereof, or a mixture of said carboxylic acid and said salt thereof and (2) an alkali metal or ammonium carbonate, alkali metal or ammonium bicarbonate, or mixtures thereof.

4. The formulation of claim 1 wherein said member (c) comprises an acetate anion or a carbonate or bicarbonate anion.

5. The formulation of claim 1 wherein said amino acid is present in an amount of about 1 mg/ml to about 50 mg/ml.

6. The formulation of claim 1 wherein said member (c) comprises at least one of an acetate anion, a carbonate anion or a bicarbonate anion, wherein said carbonate and bicarbonate anion are present at least in part from an alkali metal or ammonium carbonate, alkali metal or ammonium bicarbonate, or carbonic acid, and said acetate ion is present at least in part from an acetic acid salt or acetic acid.

7. The formulation of claim 1 packaged in a vial selected from 5 mg/vial to 500 mg/vial or in an IV infusion bag of a size selected from 25 ml/bag to about 500 ml/bag.

8. The argatroban formulation of claim 1 as a ready-to-administer aqueous solution comprising argatroban or a pharmaceutically acceptable salt thereof in an amount of at least 0.75 mg/ml (based on the argatroban moiety); lactobionic acid or a pharmaceutically acceptable salt thereof in an amount (based on the non-salt form thereof) or a mixture of said lactobionic acid and lactobionic acid salt of at least 1.5 times the weight of the argatroban (based on the argatroban moiety) and/or an alkali metal or ammonium salt or mixture of alkali metal or ammonium salts of carbonic acid or mixture of lactobionic acid salts in an amount based on $CO_3$ of at least 1.4 times the weight of the argatroban (based on the argatroban moiety); and methionine or a pharmaceutically acceptable salt thereof in an amount (based on the non-salt form of methionine) of at least 1.5 times the weight of the argatroban (based on the argatroban moiety).

9. The formulation of claim 8 wherein said argatroban or pharmaceutically acceptable salt thereof is present in an amount of about 0.75 mg/ml to about 1.25 mg/ml based on the argatroban moiety.

10. The formulation of claim 8 wherein said lactobionic acid or pharmaceutically acceptable salt thereof is present (based on the non-salt form thereof) in an amount of not more than 2.5 times the weight of the argatroban (based on the argatroban moiety) or said alkali metal or ammonium salt or mixture of alkali metal or ammonium salts of carbonic acid is present in an amount based on $CO_3$ of not more than 5.2 times the weight of the argatroban (based on the argatroban moiety).

11. The formulation of claim 8 wherein said methionine or pharmaceutically acceptable salt thereof is present (based on the non-salt form thereof) in an amount of not more than 2.5 times than weight of the argatroban (based on the argatroban moiety).

12. The formulation of claim 8 having a pH in excess of 8.6.

13. The formulation of claim 8 having a pH of about 8.7, about 8.8, about 8.9, about 9.0, about 9.1, or about 9.2.

14. The formulation of claim 8 having (1) a weight ratio of argatroban or pharmaceutically acceptable salt thereof: lactobionic acid or pharmaceutically acceptable salt thereof: methionine or pharmaceutically acceptable salt thereof (each based on the respective non-salt forms) of about 0.75 to about 1.25: about 1.50 to about 2.50: about 1.50 to about 2.50 or (2) a weight ratio of argatroban or pharmaceutically acceptable salt thereof: alkali metal or ammonium salt or mixture of alkali metal or ammonium salts of carbonic acid (based on $CO_3$): methionine or pharmaceutically acceptable salt thereof (each of the argatroban salt and amino acid salt based on the respective non-salt forms) of about 0.75 to about 1.25: about 1.4 to about 5.2: about 1.50 to about 2.50.

15. The formulation of claim 8 having
(1) a weight ratio of argatroban or pharmaceutically acceptable salt thereof: lactobionic acid or pharmaceutically acceptable salt thereof: methionine or pharmaceutically acceptable salt thereof (each based on the respective non-salt forms) of about 1: about 2: about 2 or
(2) a weight ratio of argatroban or pharmaceutically acceptable salt thereof: alkali metal or ammonium salt or mixture of alkali metal or ammonium salts of carbonic acid (based on $CO_3$): methionine or pharmaceutically acceptable salt thereof (each of the argatroban salt and methionine salt based on the respective non-salt forms) of about 1: about 4.1 about 4.2.

16. A reconstitutable formulation of argatroban comprising (a) said argatroban or a salt thereof or mixtures thereof, and
(b) methionine, pharmaceutically acceptable salts thereof, and mixtures thereof;
(c) a member selected from the group consisting of one or more non-amino acid pH adjusting organic acids or organic base or salts thereof and mixtures thereof; and
(d) a member selected from the group consisting of lactobionic acid;
which reconstitutable formulation is substantially free of a mono-, di-, or oligosaccharide and substantially free of a sugar alcohol.

17. A method of treating thrombosis comprising administering to a patient having thrombosis the composition of claim 1.

18. The method of claim 17 where said composition is in a ready-to-administer form.

19. The method of claim 17 where said composition is in the form of a concentrate and diluting said concentrate with an injectably suitable aqueous diluent to a suitable concentration for injection.

20. The formulation of claim 1 further comprising an osmolality adjuster.

21. The formulation of claim 1, further comprising a pH adjuster.

22. A pharmaceutically acceptable argatroban formulation, which is solubilized in aqueous solution, said formulation comprising (a) argatroban of formula I or a pharmaceutically acceptable salt thereof

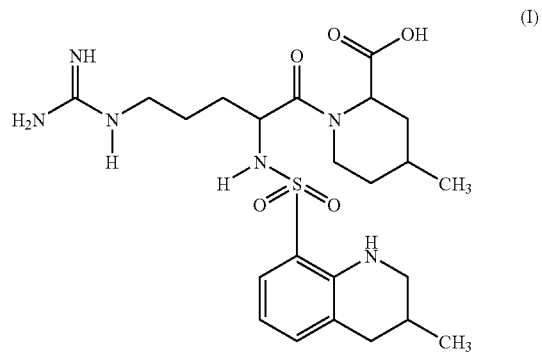

(b) methionine, pharmaceutically acceptable salts thereon and mixtures thereof;
(c) a member selected from the group consisting of one or more non-amino acid pH adjusting organic acids or organic base or salts thereof and mixtures thereof; and
(d) a member selected from the group consisting of lactobionic acid,
which formulation is substantially free of ethanol and substantially free of a sugar alcohol and has a pH in excess of 8.5.

23. The formulation of claim 22, further comprising a pH adjuster other than those materials selected from said member (b), said member (c) and said member (d) of said claim 22.

* * * * *

UNITED STATES PATENT AND TRADEMARK OFFICE
CERTIFICATE OF CORRECTION

PATENT NO.       : 7,589,106 B2
APPLICATION NO.  : 11/904067
DATED            : September 15, 2009
INVENTOR(S)      : Nageswara R. Palepu It is certified that error appears in the above-identified patent and that said Letters Patent is hereby corrected as shown below:

Column 12, line 2 in claim 8,
"lactobionie" should read --lactobionic--

Column 13, line 10 in claim 16,
delete "a member selected from the group consisting of"

Column 14, line 25 in claim 22,
delete "a member selected from the group consisting of"

Signed and Sealed this
Twenty-fourth Day of January, 2012

David J. Kappos
*Director of the United States Patent and Trademark Office*